(12) United States Patent
Maghribi et al.

(10) Patent No.: US 7,035,692 B1
(45) Date of Patent: Apr. 25, 2006

(54) HIGH DENSITY POLYMER-BASED INTEGRATED ELECTRODE ARRAY

(75) Inventors: Mariam N. Maghribi, Livermore, CA (US); Peter A. Krulevitch, Pleasanton, CA (US); James Courtney Davidson, Livermore, CA (US); Julie K. Hamilton, Tracy, CA (US)

(73) Assignee: The Regents of the University of California, Oakland, CA (US)

( * ) Notice: Subject to any disclaimer, the term of this patent is extended or adjusted under 35 U.S.C. 154(b) by 60 days.

(21) Appl. No.: 10/825,782

(22) Filed: Apr. 16, 2004

Related U.S. Application Data

(60) Provisional application No. 60/467,004, filed on Apr. 30, 2003.

(51) Int. Cl.
*A61N 1/05* (2006.01)
*A61N 1/18* (2006.01)
(52) U.S. Cl. .................. 607/53; 600/383; 623/6.63
(58) Field of Classification Search .............. 607/46, 607/53, 54, 116, 117, 129, 142, 152; 623/6.63; 600/382–383
See application file for complete search history.

(56) References Cited

U.S. PATENT DOCUMENTS

| | | | |
|---|---|---|---|
| 4,573,481 A | 3/1986 | Bullara | |
| 5,741,331 A * | 4/1998 | Pinchuk | 424/423 |
| 5,800,530 A | 9/1998 | Rizzo, III | |
| 6,052,624 A | 4/2000 | Mann | |
| 6,324,429 B1 | 11/2001 | Shire et al. | |
| 6,368,349 B1 * | 4/2002 | Wyatt et al. | 623/6.63 |
| 6,792,314 B1 * | 9/2004 | Byers et al. | 607/53 |
| 2002/0091421 A1 * | 7/2002 | Greenberg et al. | 607/54 |
| 2003/0097165 A1 | 5/2003 | Krulevitch et al. | |
| 2003/0097166 A1 | 5/2003 | Krulevitch et al. | |

\* cited by examiner

*Primary Examiner*—Carl Layno
*Assistant Examiner*—Tammie K. Heller
(74) *Attorney, Agent, or Firm*—Eddie E. Scott; Alan H. Thompson

(57) ABSTRACT

A high density polymer-based integrated electrode apparatus that comprises a central electrode body and a multiplicity of arms extending from the electrode body. The central electrode body and the multiplicity of arms are comprised of a silicone material with metal features in said silicone material that comprise electronic circuits.

15 Claims, 4 Drawing Sheets

HIGH DENSITY POLYMER-BASED INTEGRATED ELECTRODE ARRAY

CROSS-REFERENCE TO RELATED APPLICATIONS

This application claims the benefit of U.S. Provisional Patent Application No. 60/467,004 filed Apr. 30, 2003 and titled "High Density Polymer-based Integrated Electrode Array." U.S. Provisional Patent Application No. 60/467,004 filed Apr. 30, 2003 and titled "High Density Polymer-based Integrated Electrode Array" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to electrode arrays and more particularly to high density polymer-based integrated electrode arrays.

2. State of Technology

U.S. Pat. No. 4,573,481 for an implantable electrode array by Leo A. Bullara, patented Mar. 4, 1986 provides the following background information, "It has been known for almost 200 years that muscle contraction can be controlled by applying an electrical stimulus to the associated nerves. Practical long-term application of this knowledge, however, was not possible until the relatively recent development of totally implantable miniature electronic circuits which avoid the risk of infection at the sites of percutaneous connecting wires. A well-known example of this modern technology is the artificial cardiac pacemaker which has been successfully implanted in many patients. Modern circuitry enables wireless control of implanted devices by wireless telemetry communication between external and internal circuits. That is, external controls can be used to command implanted nerve stimulators to regain muscle control in injured limbs, to control bladder and sphincter function, to alleviate pain and hypertension, and to restore proper function to many other portions of an impaired or injured nerve-muscle system. To provide an electrical connection to the peripheral nerve which controls the muscles of interest, an electrode (and sometimes an array of multiple electrodes) is secured to and around the nerve bundle. A wire or cable from the electrode is in turn connected to the implanted package of circuitry."

U.S. Pat. No. 6,052,624 for a directional programming for implantable electrode arrays by Carla M. Mann, patented Apr. 18, 2000 provides the following background information, "Within the past several years, rapid advances have been made in medical devices and apparatus for controlling chronic intractable pain. One such apparatus involves the implantation of an electrode array within the body to electrically stimulate the area of the spinal cord that conducts electrochemical signals to and from the pain site. The stimulation creates the sensation known as paresthesia, which can be characterized as an alternative sensation that replaces the pain signals sensed by the patient. One theory of the mechanism of action of electrical stimulation of the spinal cord for pain relief is the "gate control theory." This theory suggests that by simulating cells wherein the cell activity counters the conduction of the pain signal along the path to the brain, the pain signal can be blocked from passage. Spinal cord stimulator and other implantable tissue stimulator systems come in two general types: "RF" controlled and fully implanted. The type commonly referred to as an "RF" system includes an external transmitter inductively coupled via an electromagnetic link to an implanted receiver that is connected to a lead with one or more electrodes for stimulating the tissue. The power source, e.g., a battery, for powering the implanted receiver-stimulator as well as the control circuitry to command the implant is maintained in the external unit, a hand-held sized device that is typically worn on the patient's belt or carried in a pocket. The data/power signals are transcutaneously coupled from a cable-connected transmission coil placed over the implanted receiver-stimulator device. The implanted receiver-stimulator device receives the signal and generates the stimulation. The external device usually has some patient control over selected stimulating parameters, and can be programmed from a physician programming system."

U.S. Pat. No. 6,230,057 for a multi-phasic microphotodiode retinal implant and adaptive imaging retinal stimulation system by Vincent Chow and Alan Chow, patented May 8, 2001 and assigned to Optobionics Corporation provides the following background information, "A variety of retinal diseases cause vision loss or blindness by destruction of the vascular layers of the eye including the choroid, choriocapillaris, and the outer retinal layers including Bruch's membrane and retinal pigment epithelium. Loss of these layers is followed by degeneration of the outer portion of the inner retina beginning with the photoreceptor layer. Variable sparing of the remaining inner retina composed of the outer nuclear, outer plexiform, inner nuclear, inner plexiform, ganglion cell and nerve fiber layers, may occur. The sparing of the inner retina allows electrical stimulation of this structure to produce sensations of light. Prior efforts to produce vision by electrically stimulating various portions of the retina have been reported. One such attempt involved an externally powered photosensitive device with its photoactive surface and electrode surfaces on opposite sides. The device theoretically would stimulate the nerve fiber layer via direct placement upon this layer from the vitreous body side. The success of this device is unlikely due to it having to duplicate the complex frequency modulated neural signals of the nerve fiber layer. Furthermore, the nerve fiber layer runs in a general radial course with many layers of overlapping fibers from different portions of the retina. Selection of appropriate nerve fibers to stimulate to produce formed vision would be extremely difficult, if not impossible. Another device involved a unit consisting of a supporting base onto which a photosensitive material such as selenium was coated. This device was designed to be inserted through an external scleral incision made at the posterior pole and would rest between the sclera and choroid, or between the choroid and retina. Light would cause a potential to develop on the photosensitive surface producing ions that would then theoretically migrate into the retina causing stimulation. However, because that device had no discrete surface structure to restrict the directional flow of charges, lateral migration and diffusion of charges would occur thereby preventing any acceptable resolution capability. Placement of that device between the sclera and choroid would also result in blockage of discrete ion migration to the photoreceptor and inner retinal layers. That was due to the presence of the choroid, choriocapillaris, Bruch's membrane and the retinal pigment epithelial layer all of which would block passage of those ions. Placement of the device between the choroid and the retina would still interpose Bruch's membrane and the retinal pigment epithelial layer in the pathway of discrete ion migration. As that device would be inserted into or through the highly vascular choroid of the posterior pole, subchoroidal, intraretinal and intraorbital hemorrhage would likely result along with disruption of blood flow to the posterior pole. One such device was reportedly constructed and implanted into a patient's eye resulting in light perception but not formed imagery. A photovoltaic device artificial retina was also disclosed in U.S. Pat. No. 5,024,223. That device was inserted into the potential space within the retina itself. That space, called the subretinal space, is located between the outer and inner layers of the retina. The device was comprised of a plurality of so-called Surface Electrode Microphotodiodes ("SEMCPs") deposited on a single silicon crystal substrate. SEMCPs transduced light into small electric currents that stimulated overlying and surrounding inner retinal cells. Due to the solid substrate nature of the SEMCPs, blockage of nutrients from the choroid to the inner retina occurred. Even with fenestrations of various geometries, permeation of oxygen and biological substances was not optimal. Another method for a photovoltaic artificial retina device was reported in U.S. Pat. No. 5,397,350, which is incorporated herein by reference. That device was comprised of a plurality of so-called Independent Surface Electrode Microphotodiodes (ISEMCPs), disposed within a liquid vehicle, also for placement into the subretinal space of the eye. Because of the open spaces between adjacent ISEMCPs, nutrients and oxygen flowed from the outer retina into the inner retinal layers nourishing those layers. In another embodiment of that device, each ISEMCP included an electrical capacitor layer and was called an ISEMCP-C. ISEMCP-Cs produced a limited opposite direction electrical current in darkness compared to in the light, to induce visual sensations more effectively, and to prevent electrolysis damage to the retina due to prolonged monophasic electrical current stimulation. These previous devices (SEMCPs, ISEMCPs, and ISEMCP-Cs) depended upon light in the visual environment to power them. The ability of these devices to function in continuous low light environments was, therefore, limited. Alignment of ISEMCPs and ISEMCP-Cs in the subretinal space so that they would all face incident light was also difficult."

U.S. Pat. No. 6,324,429 for a chronically implantable retinal prosthesis by Doug Shire, Joseph Rizzo, and John Wyatt, of the Massachusetts Eye and Ear Infirmary Massachusetts Institute of Technology issued Nov. 27, 2001 provides the following information, "In the human eye, the ganglion cell layer of the retina becomes a monolayer at a distance of 2.5–2.75 mm from the foveal center. Since the cells are no longer stacked in this outer region, this is the preferred location for stimulation with an epiretinal electrode array. The feasibility of a visual prosthesis operating on such a principle has been demonstrated by Humayun, et al. in an experiment in which the retinas of patients with retinitis pigmentosa, age-related macular degeneration, or similar degenerative diseases of the eye were stimulated using bundles of insulated platinum wire. The patients were under local anesthesia, and they described seeing points of light which correctly corresponded with the region of the retina in which the stimulus was applied (Humayun, M., et al., Archiv. Ophthalmol., 114: 40–46, 1996). The form of the stimulating device was, however, not suited for chronic implantation. The threshold for perception was reported to be in the range of 0.16–70 mC/cm.sup.2. This confirmed the results of earlier experiments on animal subjects by the instant inventors and others which indicated that strong evoked cortical potentials could be observed when rabbit retinas were stimulated using passive microfabricated electrode arrays similar in some respects to the ones proposed in the current invention (Rizzo, J. F., et al., ARVO Poster Session Abstract, Investigative Ophthalmology and Visual Science, 37: S707, 1996; Walter, P., et al. Investigative Ophthalmology and Visual Science, 39: S990, 1998). The instant inventors have, with others, performed three surgical procedures using microfabricated electrode arrays and similar in technique to those described by Humayun and confirmed that a consistent response to input electrical stimuli could be noted by the patient. The task of creating a retinal implant has been addressed by Chow, in U.S. Pat. No. 5,016,633, who proposed a subretinal implant based on a microphotodiode array. The procedure involved in its implantation is so biologically intrusive, however, that successful implementation of such a device in human subjects has not been reported. Furthermore, an entirely passive array will be rather insensitive under normal lighting conditions, and an array powered from outside the body by means of a direct electrical connection will likely lead to infections and again, be so intrusive as to be objectionable. Earlier designs of the present inventors placed all components of the prosthesis on the retinal surface (U.S. patent application Ser. No. 19/074,196, filed May 7, 1998, and U.S. Pat. No. 5,800,530, both of which are incorporated herein by reference). It became quickly apparent that the delicate retina could not withstand the mechanical burden which was at least partially the result of the relatively thick profile of the microelectronic components. A later prototype included one significant change in design—the bulky microelectronic components were moved anteriorly within the eye, off of the retinal surface. In this configuration, the microelectronics are held in a custom-designed intraocular lens, and only a thin ribbon containing the microelectrodes extends rearwardly to the retinal surface."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a high density polymer-based integrated electrode apparatus. The apparatus comprises a central electrode body and a multiplicity of arms extending from the electrode body. The central electrode body and the multiplicity of arms are comprised of a silicone material with metal features in said silicone material that comprise electronic circuits. The present invention provides increased density of electrodes to meet increased resolution requirements needed for electrical devices such as artificial vision and hearing implants.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
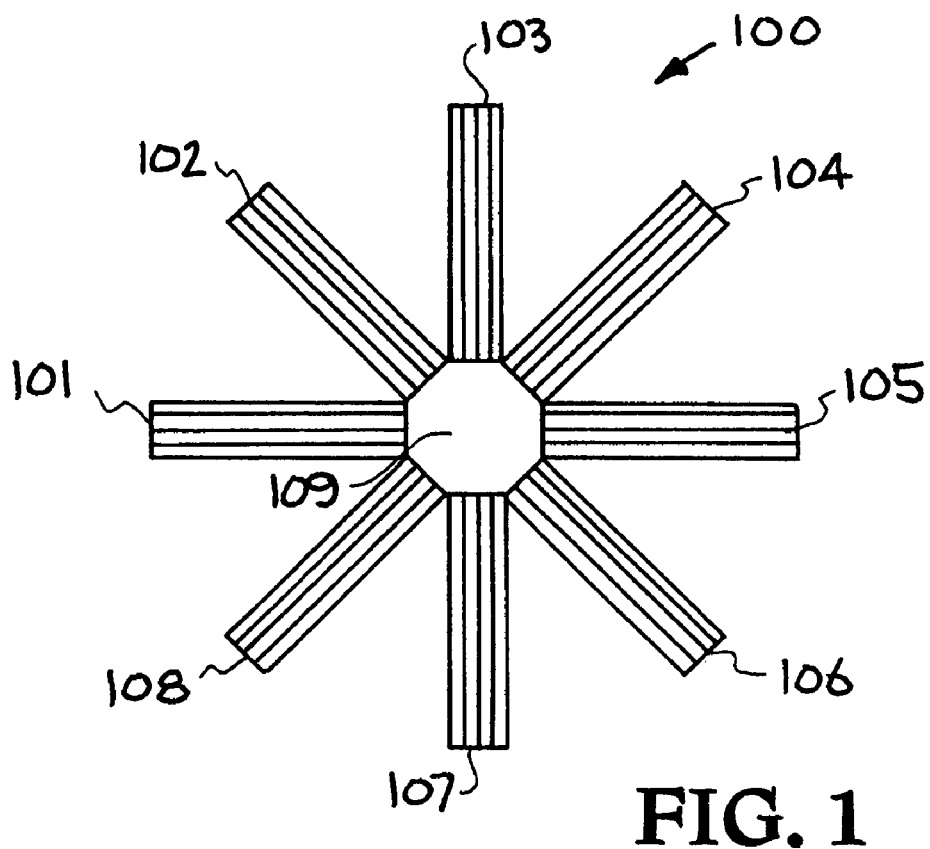
FIG. 1 embodiment of a system constructed in accordance with the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 2:
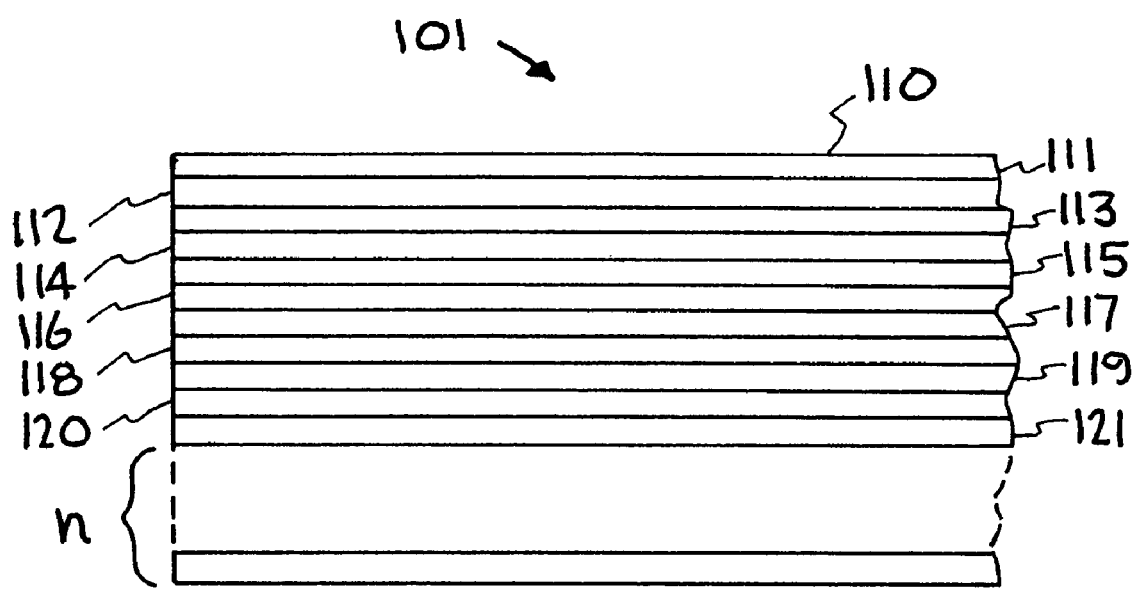
FIG. 2 shows one of the tabs or arms that contains the metal traces in a substrate composed of a polymer.
Figures 3, 4:
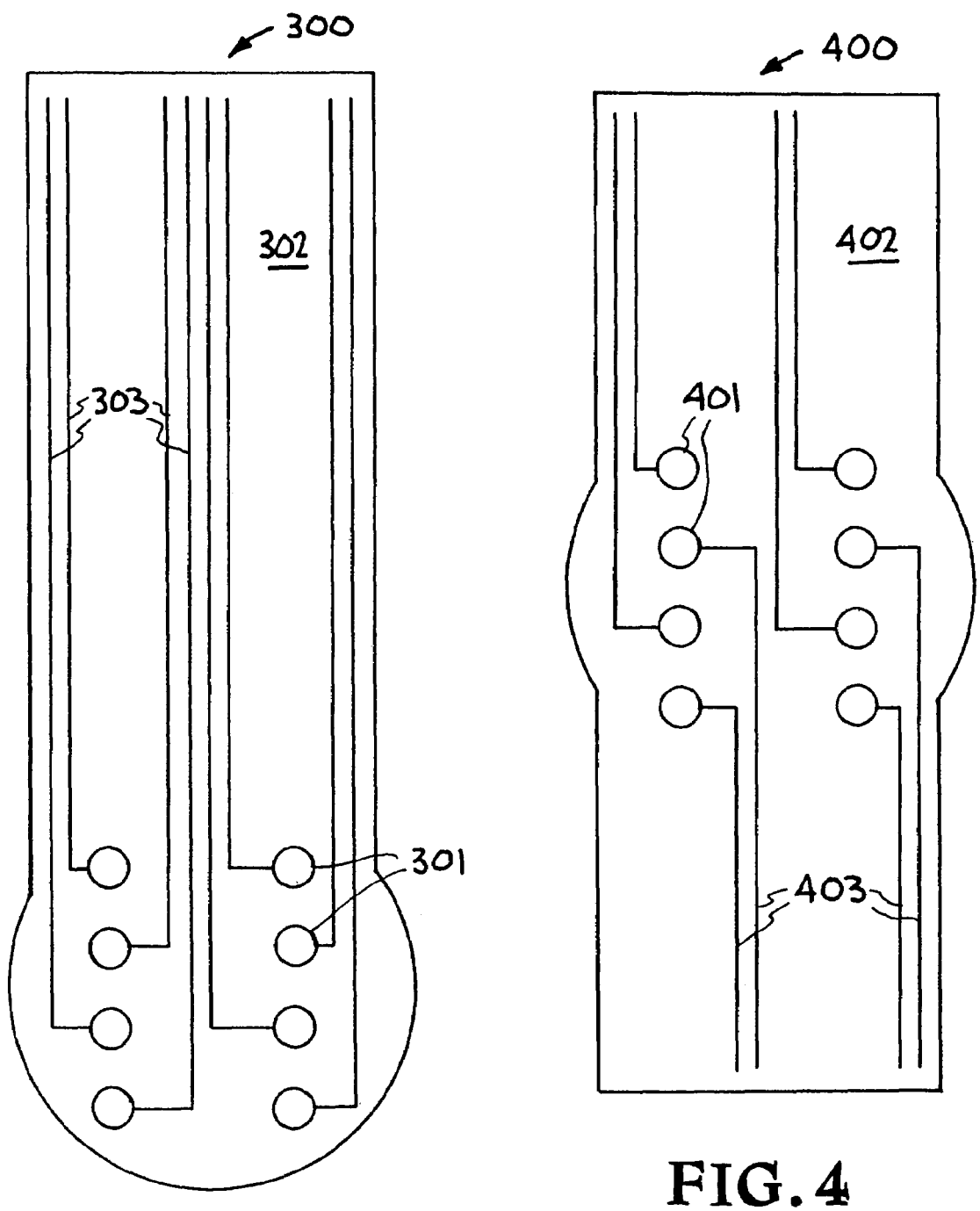
FIG. 3 illustrates an embodiment showing how the metal traces are connected through the central electrode array.
FIG. 4 illustrates another embodiment showing how the metal traces are connected through the central electrode array.

Referring now to FIGS. 1, 2, and 3, an embodiment of a system constructed in accordance with the present invention is illustrated. The system is designated generally by the reference numeral 100. The system 100 provides a significant number of electrodes contained within a small area. The system 100 provides increased density of electrodes to meet increased resolution requirements needed for electrical devices such as artificial vision and hearing implants. By way of example, the system 100 meets increased resolution requirements that require placing 1000 electrodes in a 4×4 mm area.

As illustrated in FIG. 1, a multiplicity of tabs or arms radiate from a central electrode array 109. Tabs or arms 101 through 108 are shown in FIG. 1. The central electrode array 109 contains the conducting metallization required to energize each individual electrode.

The individual tabs or arms contain separate metal traces for electrical contact. As illustrated in FIG. 2, the arm 101 contains separate metal traces, 111 through n, for electrical contact. Depending on the desired size of the individual electrodes each tab or arm contains from one to a predetermined number of separate metal traces.

Referring now to FIG. 3 one embodiment of a system is illustrated wherein the metal traces are connected through the central electrode array and contain the conducting metallization required to energize each individual electrode. The embodiment is designated generally by the reference numeral 300.

The system 300 provides electrodes 301 contained in a polymer substrate 302. The substrate 302 is composed of a polymer. The polymer has the ability to conform to various shapes of the tissue. The polymer in the embodiment 300 is poly(dimethylsiloxane) or PDMS. Metal traces 303 are provided for electrical connection. The metal traces 303 in the embodiment 300 are composed of lead metal.

The production of a substrate that can be used as the poly(dimethylsiloxane) or PDMS substrate 302 and production of metal traces that can be used as the metal traces 303 is described in U.S. Patent Application No. 2003/0097166 by Peter Krulevitch, Dennis L. Polla, Mariam Maghribi, and Julie Hamilton for a Flexible Electrode Array for Artificial Vision published May 22, 2003; U.S. Patent Application No. 2003/0097165 by Peter Krulevitch, Dennis L. Polla, Mariam Maghribi, Julie Hamilton, and Mark S. Humayun for a Flexible Electrode Array for Artificial Vision published May 22, 2003; and U.S. Patent Application No. 2004/0018297 by Courtney Davidson, Peter Krulevitch, Mariam Maghribi, William Benett, Julie Hamilton, and Armando Tovar for Conductive Inks for Metalization in Integrated Polymer Microsystems published Jan. 29, 2004. U.S. Patent Applications Nos. 2003/0097166, 2003/0097165, and 2004/0018297 are incorporated herein in their entirety by this reference.

The system 100 has many uses. For example, the system 100 has uses for implantable, biocompatible electrode arrays; biological, chemical, temperature, radiation sensor; sensors and stimulators for interfacing with human body and inanimate objects; non-destructive evaluation sensors; flexible display monitors; smart notes; and monitoring devices. The system 100 also has uses for implantable devices: epiretinal, subretinal, and cortical artificial vision implant, cochlear implants, neurological implants, spinal cord implants and other neural interface implants; implantable electrode array devices; monitoring devices; implantable ribbon cables and electrode array for deep brain stimulation, spinal cord reattachment, nerve regeneration, cortical implants, retinal implants, cochlear implants, drug delivery, muscle stimulation and relaxation; and flexible displays and smart notes, conformable circuits.

The system 100 provides an electrode array system with embedded electrodes and conductive leads that can be used for directly stimulating cells. U.S. Patent Applications Nos. 2003/0097165 and 2003/0097166 show electrode array systems. The systems use a substrate with embedded electrodes and conductive leads for directly stimulating cells. The disclosures of U.S. Patent Applications Nos. 2003/0097165 and 2003/0097166 are incorporated herein by reference.

The system 100 can provide a system that is implantable and can be used for surgical insertion. The system 100 can also be attached to the surface of the skin or other tissue. The system 100 can be used in other ways. Other applications of the system 100 include use as a flex circuit. The system 100 has uses including shaped acoustic sensors and transmitters and formed biological sensors and stimulators for interfacing with the human body. These can be used for applications ranging from non-destructive evaluation to sensors for virtual reality simulators. An implantable electrode array is shown in U.S. Pat. No. 4,573,481 by Leo A. Bullara, patented Mar. 4, 1986. The disclosure of this patent is incorporated herein in its entirety by reference. A directional programming for implantable electrode arrays is shown in U.S. Pat. No. 6,052,624 for by Carla M. Mann, patented Apr. 18, 2000. The disclosure of this patent is incorporated herein in its entirety by reference. A multi-phasic microphotodiode retinal implant and adaptive imaging retinal stimulation system, patented May 8, 2001, is shown in U.S. Pat. No. 6,230,057 by Vincent Chow and Alan Chow. The disclosure of this patent is incorporated herein in its entirety by reference. A photovoltaic artificial retina device is in U.S. Pat. No. 5,397,350. The disclosure of this patent is incorporated herein in its entirety by reference.

OctoPDMS—One specific embodiment of the invention has been designated "OctoPDMS." The embodiment utilizes metal features on Poly(dimethylsiloxane) a type of silicone rubber know as PDMS. An electrode array is contained in an octagonal base with eight tabs or arms extending from the octagonal base. The embodiment is produced by fabricating stretchable metal traces on PDMS (silicone).

The OctoPDMS embodiment will be described using FIGS. 1, 2, 3, 4, and 5. As illustrated in the figures, the OctoPDMS system is designated generally by the reference numeral 100. The OctoPDMS system 100 provides one thousand electrodes contained within an area of 16 $mm^2$. The electrode array is contained in the octagonal base 109 with eight tabs or arms 101 through 108, containing 125 metal traces 111 through n, for electrical contact, where n=the remaining metal traces to equal 125.

As illustrated by FIG. 2, the tab or arm 101 contains 125 metal traces 111 through n, for electrical contact, where n=the remaining metal traces. The tab or arm 101 includes a substrate composed of a polymer. The polymer has the ability to conform to various shapes of the tissue. The polymer is poly(dimethylsiloxane) or PDMS.

As illustrated by FIG. 3, the metal traces, 111 through n, are connected through the central electrode array 109 and contain the conducting metallization required to energize each individual electrode.

The OctoPDMS system 100 is produced by implementing various processing steps on a substrate. A description of a system for manufacturing the tab or arm 101 is described in U.S. Patent Applications Nos. 2003/0097165 and 2003/0097166 and the disclosures of U.S. Patent Applications Nos. 2003/0097165 and 2003/0097166 are incorporated herein by reference. A conductive material is deposited on a handle wafer and various processing steps are taken to complete the OctoPDMS system 100.

The OctoPDMS system 100 is produced using a number of processing steps. The OctoPDMS system 100 provides a process for depositing metal features on Poly(dimethylsiloxane) which is a type of silicone rubber. With the process Applicants are capable of fabricating stretchable metal traces on PDMS (silicone) using a cost effective batch fabrication process. Applicants have demonstrated selective passivation of these metal traces with PDMS exposing the traces only in areas needed to make contact with the outside world. The embodiment includes improvements in the process of metalizing PDMS, selective passivation, using batch fabrication photolithographic techniques to fabricate PDMS, and producing stretchable metal traces that are capable of withstanding strains of 7% with S.D. 1.

Referring now to FIG. 4 another embodiment of a system is illustrated wherein the metal traces are connected through the central electrode array and contain the conducting metallization required to energize each individual electrode. The embodiment is designated generally by the reference numeral 400.

The system 400 provides electrodes 401 contained in a polymer substrate 402. The substrate 402 is composed of a polymer. The polymer has the ability to conform to various shapes of the tissue. The polymer in the embodiment 400 is poly(dimethylsiloxane) or PDMS. Metal traces 403 are provided for electrical connection. The metal traces 403 in the embodiment 400 are composed of lead metal.

Figure 5:
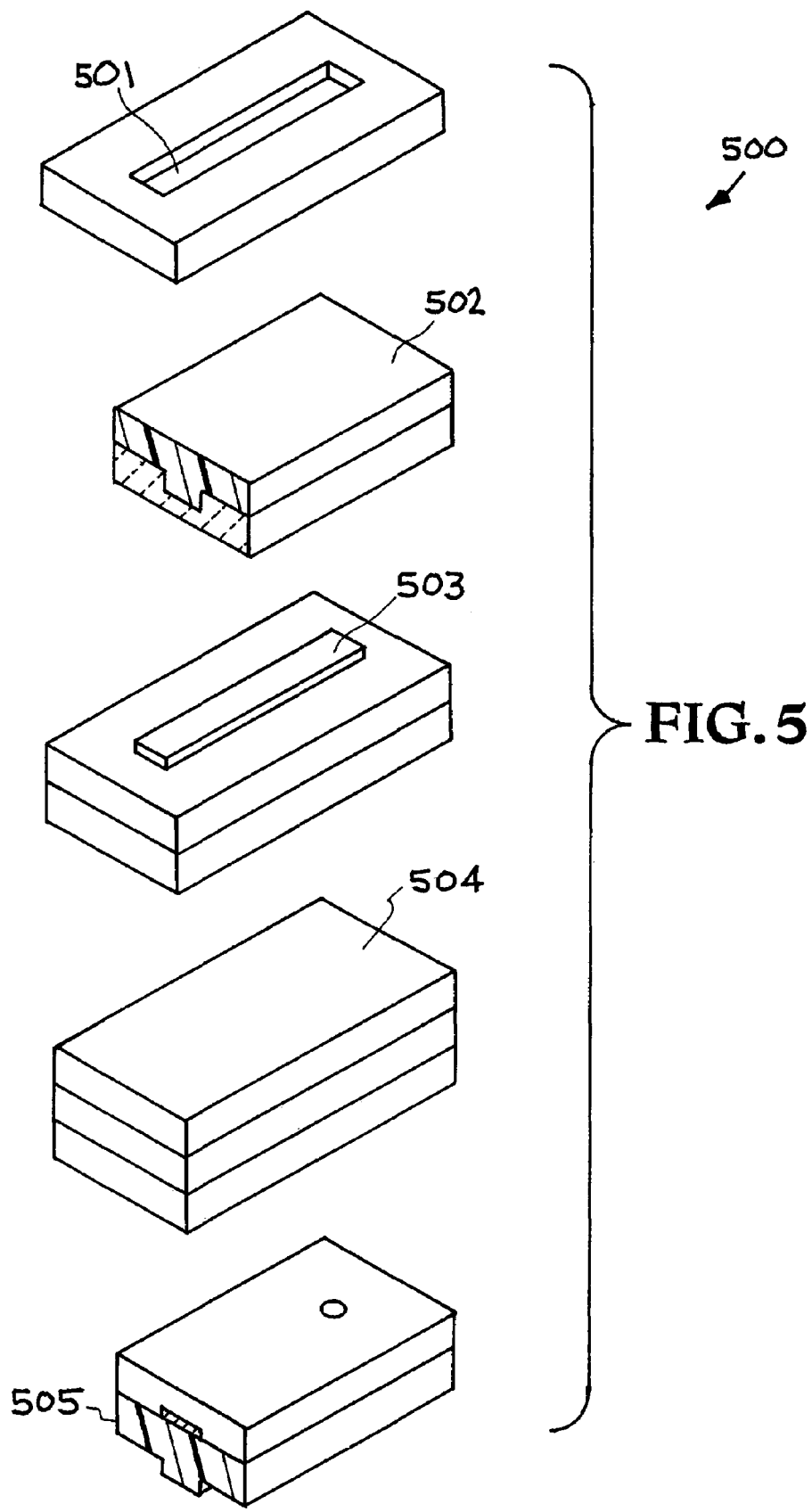
FIG. 5 illustrates process steps for depositing lead and electrode metal on PDMS and subsequent passivation with PDMS.

Referring now to FIG. 5, the basic process steps for depositing lead and electrode metal on PDMS and subsequent passivation with PDMS is illustrated. The process is designated generally by the reference numeral 500. The system 500 includes the steps of casting 501, spin 502, metallization 503, spin coating 504, and release 505. Applicants approach is to use PDMS as the substrate material to batch produces a low-cost device that is ready for implantation without the need for additional packaging steps. Because PDMS has not previously been used in this type of micromachining application, applicants developed new fabrication processes enabling PDMS patterning, metalization, and selective passivation. The metal features are embedded (deposited) within a thin substrate fabricated using poly (dimethylsiloxane) (PDMS), an inert biocompatible elastomeric material that has simultaneously low water and high oxygen permeability. The conformable nature of PDMS is critical for ensuring uniform contact with the curved surfaces.

PDMS is a form of silicone rubber, a material that is used in many implants and has been demonstrated to withstand the body's chemical and physical conditions without causing adverse side effects and is a favorable material to implant within the body. Robustness of the metalized PDMS is another important design criterion that applicants considered, as stretching and bending occur during fabrication and implantation of the device. The PDMS metalization process was demonstrated to produce devices that will be sufficiently rugged for implantation, with a demonstrated strain to failure of 7%, (SD=1). Applicants attribute the stretchability to a tensile residual stress from curing the PDMS.

In one of the initial steps, silicone is spun onto a silicon handle wafer. The silicone is poly(dimethylsiloxane) known as PDMS. PDMS has very low water permeability and protects the electronic components from the environment. PDMS is flexible and will conform to curved surfaces. It is transparent, stretchable, resinous, rubbery, stable in high temperatures and provides numerous applications for the electronic devices produced by the method 500.

The silicon handle wafer provides a temporary base for production of the electronic device. Silicon wafers are convenient for the handle material because they are flat, stable, routinely used in microfabrication applications, and they are readily available. However, other materials such as glass, plastic, or ceramic could be used as well. The electronic devices will eventually need to be removed from the handle wafer. Since the flexible polymer layer would become permanently bonded to the surface of the silicon handle wafer, a non-stick layer is first provided on the silicon handle wafer. The step comprises the deposition of gold (or platinum) onto the handle wafer. This allows for removal of the PDMS from the substrate after processing. The gold film facilitates removal of the polymer membrane from the wafer after completion of the fabrication process. Needed areas on the silicon wafer is left without the gold coating to prevent the PDMS membrane from lifting off during processing for example a 2 mm wide ring a the edge is left uncoated with gold. PDMS is then spun onto the wafer at a desired thickness and cured. For example the PDMS may be cured at 66° C. for 24–48 hours (or at manufactures' specifications). It is to be understood that the step 501 could be omitted if the surface on which the PDMS layer is deposited is such that the PDMS will not become bonded.

In a subsequent step 503 the process of forming the electrical circuit lines and the central electrode array of the OctoPDMS system 100 is initiated. A photoresist (AZ®1518, Clariant) is spun onto the PDMS membrane surface at 1000 rpm for 20 seconds and baked at 60° C. for 45 minutes. The temperature is brought down slowly (30 min. to ramp temperature down) to room temperature to avoid cracking in the photoresist. Prior to photoresist application, the wafer is placed in an oxygen plasma to activate the surface. This allows the resist to wet the PDMS surface preventing beading and ensuring the formation of a smooth and uniform coat of photoresist on the polymer surface. The substrate is placed in the oxygen plasma for 1 minute at an RF power of 100 Watts with oxygen flowing at 300 sccm. The photoresist features are then UV exposed at 279 mJ and developed in AZ developer mixed 1:1 with water for 70 sec. Then the wafer is rinsed under a gentle stream of water and dried using N2. The wafer is placed for a second time in the oxygen plasma to activate the newly exposed PDMS surface, and promote adhesion of the metal, which is deposited in the next step.

In the next step a 150 nm gold film is e-beam evaporated onto the wafer using titanium as the adhesion layer. The e-beam needs to be sufficiently cooled down before removing the parts. Cool down is conducted for 10 min. under vacuum and for 20 min. with the system vented, but not open. The metal adheres to the PDMS surface in regions where the photoresist was removed, and the excess metal is removed through a lift-off process by placing the wafer in acetone. The wafer is then prepared for the next step by rinsing with ethanol and drying gently. If the PDMS surface is contaminated or aged, it can be refreshed by soaking in a 20% solution of HCl for 8 min.

In the next steps the process of forming the vias through a passivating layer of PDMS to connect the electrical circuit lines to the electronic components of the OctoPDMS system 100 is initiated. A thick photoresist is spun onto the PDMS membrane surface. The photoresist is patterned by exposing the resist to UV through a photomask and developing. The passivating layer of silicone is spun onto the wafer, over the patterned photoresist. The surface is gently swabbed to remove excess PDMS from the top of the photoresist features before stripping the resist. This ensures the removal of the photoresist and the complete clearance of the vias. To strip the resist the wafer is soaked in acetone for 15 min. and then soaked in isoproponol for 5 min. and then rinsed with isoproponol and dried.

Another way of patterning and passivating the PDMS is using a shadow-mask, which is a stencil-like mask exposing the areas that need to be passivated or patterned. A third way of passivating the PDMS is by protecting the areas needed for electrical connection and dipping the wafer in PDMS and curing.

In the next step conductive material is applied to the vias. The vias can be filled with electroplating, conductive silicone adhesive, conductive ink or solder paste. An automated dispenser or applicator machine is used to deposit precise amounts of material in the vias locations. Alternatively, the conductive material can be screen-printed using conductive inks, or liquid ink can be injected into channels formed in the first PDMS layer. As another option, metal can be electroplated in the PDMS vias to form an array of electrical contacts.

In the next step, the surface of the second PDMS layer is rinsed with ethanol and exposed to an oxygen plasma. This activates the surface in preparation for bonding the electronic components to the PDMS. The following step is performed in a nitrogen environment in order to extend the lifetime of the activated surface.

Figure 6:
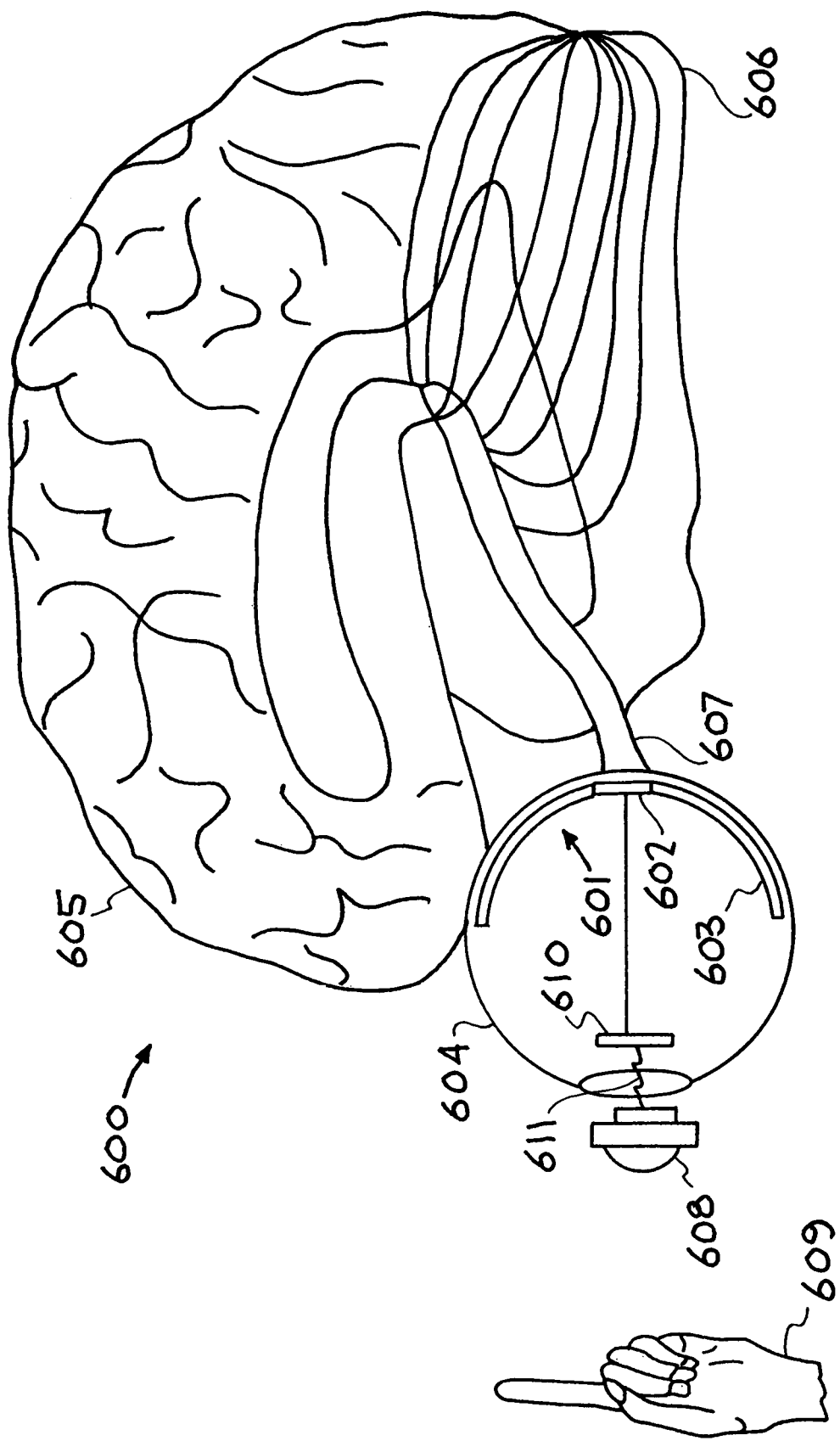
FIG. 6 illustrates a system that restores vision to people with certain types of eye disorders.

Referring now to FIG. 6, an embodiment of a system constructed in accordance with the present invention is illustrated. The system is designated generally by the reference numeral 600.

The system 600 provides a system that restores vision to people with certain types of eye disorders. The system 600 includes a video camera 608 that captures an image 609. A device sends the image via a cable connection, a laser or RF signal 611 into a patient's eye 604. Electronics, generally indicated by the reference numeral 601 within the eye 604 receives the image 609 signal and send it to the electrode array designated by the reference numerals 602 and 603. The electrode array 602 and 603 utilizing a substrate made of a compliant material with electrodes and conductive leads embedded in a substrate. The electrodes contact tissue of the retina. The implant electronics 601 stimulates retinal neurons. The retinal neurons transmit a signal to the brain 605.

The system 600 provides an artificial vision system that can help restore vision to people left totally or partially blind by retinal degeneration or other retinal diseases. In retinitis pigmentosa (RP), the progression of the disease can be slow, but eventually can lead to total blindness. However, some of the visual cortex 606 and some of the optic nerve cells 607 remain viable, and it may be possible to restore vision through stimulation of these cells.

Referring again to FIG. 6, the video camera 608 captures the image 609. The image is sent via wire, a laser or RF signal 52 into the eye 604 to the implant 610. The implant 610 is connected to the retina by electrodes 601. The implant 610 stimulates retinal neurons. The retinal neurons transmit the signal to be decoded. The system senses an image and stimulates the retina with a pattern of electrical pulses based on the sensed image signal.

The implant 610 includes the electrode array 601 of poly(dimethylsiloxane) (PDMS, a form of silicone rubber) for the substrate. The substrate includes embedded electrodes and conductive leads for directly stimulating cells in the retina and transmitting a visual image. The fact that the device is flexible and can conform to the shape of the patient's retina is highly advantageous. The device is stretchable, making it rugged during handling, insertion, and use. PDMS is oxygen-permeable but absorbs very little water, two properties that are advantageous for a biological implant. PDMS is an example of a material that works well for this application, but other polymers also could be used.

The flexible, stretchable electrode array 601 has many uses, including shaped acoustic transducers, and formed biological sensors and stimulators for interfacing with the human body. These can be used for applications ranging from non-destructive evaluation to sensors and stimulators for virtual reality simulators. The engineering characteristics described below are included in the implantable electrode array 601.

Platinum electrodes with photolithographically defined features including micron-scale contacts for precision stimulation, tailored impedance for overall systems matching requirements.

A flexible biocompatible electrode substrate that can be easily inserted and positioned according to the contour of the inner eye.

An electrical interconnection array for interfacing with a regulated current drive derived from the processed image of the receiver chip. This consists of a micromachined conformable electrode surface hybrid-bump bonded to a second RF control circuit that applies electrical signals derived from the sensed image. The electronics chip can be embedded in the PDMS, forming a single, integrated, implantable device.

All electrical leads and circuits except the electrode contacts will be embedded in the PDMS substrate. Thus, the PDMS forms a biocompatible package. Another approach is to attach the PDMS electrode array to a hermetically sealed electronics package.

Materials such as platinum, titanium, and iridium oxide can be prepared by sputtering, electron beam evaporation, and electroplating. An important approach described for fabricating the above neurostimulator array lies in the use of PDMS as the starting material substrate. The conformable nature of the PDMS material is important in order to ensure stable and uniform mechanical contact with retinal tissue. Technical approaches based on the use of traditional silicon substrates are limited due to the mechanical rigidity and fragility of silicon.

Experience in processing this material for other BioMEMS applications have shown this material to be remarkably easy to deposit, pattern, and handle. PDMS allows the mechanical flexibility, robustness, and stretchability required for placement in full area contact according to the shape of the retina. Attachment holes for sutures or tacks can easily be formed in the PDMS substrate by simple spacer castings. In addition, barbs or hooks or tacks can be formed on the surface of the PDMS using a suitable mold, or can be made of other materials and embedded within the PDMS.

Electrical interconnection between the stimulation electrode array and front-end electronics presents unique challenges in this implantable biomedical device application. For the retinal prosthesis application an encoded RF broadcast signal is used to communicate an image pattern to a multiplexor. The multiplexor in turn sets a pattern on temporal current pulses that drives the electrode array. The main advantage of this approach lies in the use of a short-range RF broadcast signal (~1 cm). This eliminates the need for mechanical wire interconnections that are subject to failure and present significant packaging problems. A second RF signal applied external to the eye is used to charge storage capacitors that ultimately deliver current to the electrode array.

Electrode interconnections are mechanically robust to prevent breakage, exhibit characteristics of an ideal electrical conductor, and provide isolation from the biological environment within the eye. Bump bonding the integrated circuit chip onto the microelectrode array device, then encapsulating in PDMS addresses both of these issues. The IC chip can be directly bonded to the back of the electrode array, with an optional interface chip, or can be bonded to the side of the electrode array with conducting leads delivering the signal to the electrodes.

The base will lie against the retina while the arms conform to the curvature of the eye and converge onto an IC chip in the region where the lens usually resides.

The final implant specifications calls for a device with approximately 1000 electrodes contained within an area of 16 mm$^2$. The electrode array is contained in the octagonal base with eight arms containing 125 metal traces for electrical contact.

The central portion of the device contains an arbitrary number of electrodes. The tabs radiating from the central electrode array contain the conducting metallization required to energize each electrode. Depending on the size of the individual electrodes each tab may contain from one to an arbitrary number. (While this describes eight connections to the array it is easy to extend this approach to an arbitrary number of connectors, each containing an arbitrary number of conductors.)

Long-term biocompatibility studies are currently being performed to ensure life long durable implants. The main obstacle to the implantation will be the maintenance of the implant inside the body. It is prerequisite that the implant remains viable and biocompatible for the entire life of the recipient.

The medical purpose of the retinal implant is strictly to give enough sight to the blind in order to make their lives more self-sufficient. Researchers are exploring and have yet to discover methods to provide depth perception, color, and contrast to the images created by the implant. A grand challenge still exists to develop an implant capable of providing complete natural vision. However the great success of the cochlear implant is proof that a neural implant can make a significant impact despite its simplicity in comparison to natural biological system. There is no doubt that an implantable retina will have a significant impact on our society as it helps to alleviate some forms of blindness. Providing sight to the visually impaired through retinal prosthesis will be a phenomenal application of polymer-based microtechnology.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A high density polymer-based integrated electrode apparatus, comprising:
   a central electrode body, and
   a multiplicity of arms extending from said electrode body, wherein said central electrode body and said multiplicity of arms are comprised of a silicone material with metal features in said silicone material that comprise electronic circuits and wherein said arms comprise a silicone material with 125 separate metal traces in said silicone material.

2. The high density polymer-based integrated electrode apparatus of claim 1 wherein said silicone material is poly(dimethylsiloxane).

3. The high density polymer-based integrated electrode apparatus of claim 1 wherein said arms comprise a silicone material with 1 through n separate metal traces in said silicone material.

4. The high density polymer-based integrated electrode apparatus of claim 1 wherein said arms comprise a poly(dimethylsiloxane) material with a multiplicity of separate metal traces in said poly(dimethylsiloxane) material.

5. The high density polymer-based integrated electrode apparatus of claim 1 wherein said arms comprise a poly(dimethylsiloxane) material with 1 through n separate metal traces in said poly(dimethylsiloxane) material.

6. The high density polymer-based integrated electrode apparatus of claim 1 wherein said arms comprise a poly(dimethylsiloxane) material with one hundred twenty five separate metal traces in said poly(dimethylsiloxane) material.

7. The high density polymer-based integrated electrode apparatus of claim 1 comprising eight separate arms made of a silicone material and one hundred twenty five separate metal traces in said silicone material of each of said eight separate arms.

8. The high density polymer-based integrated electrode apparatus of claim 1 comprising eight separate arms made of a poly(dimethylsiloxane) material and one hundred twenty five separate metal traces in said poly(dimethylsiloxane) material of each of said eight arms.

9. The high density polymer-based integrated electrode apparatus of claim 1 comprising eight separate arms made of a silicone material and one hundred twenty five separate metal traces in said silicone material of each of said eight separate arms, said eight separate arms and said central electrode body contained within an area of 16 mm$^2$.

10. The high density polymer-based integrated electrode apparatus of claim 1 comprising eight separate arms made of a poly(dimethylsiloxane) material and one hundred twenty five separate metal traces in said poly(dimethylsiloxane) material of each of said eight arms, said eight separate arms and said central electrode body contained within an area of 16 mm$^2$.

11. The high density polymer-based integrated electrode apparatus of claim 1 comprising one thousand electrical circuits within an area of 16 mm$^2$ and contained in eight separate arms made of a silicone material and one hundred twenty five separate metal traces in said silicone material of each of said eight separate arms.

12. The high density polymer-based integrated electrode apparatus of claim 1 comprising one thousand electrical circuits within an area of 16 mm$^2$ and contained in eight separate arms made of a poly(dimethylsiloxane) material and one hundred twenty five separate metal traces in said poly(dimethylsiloxane) material of each of said eight arms.

13. The high density polymer-based integrated electrode apparatus of claim 1 for capturing an image and transmitting the image into an eye to a brain, the apparatus including a video camera that captures the image and sends the image to the eye and through separate metal traces in said arms and said central electrode body to the brain.

14. The high density polymer-based integrated electrode apparatus of claim 1 for capturing an image and transmitting the image into an eye to a brain, the apparatus including a video camera that captures the image and sends the image to the eye and through separate metal traces in separate arms made of a poly(dimethylsiloxane) and said central electrode body to the brain.

15. The high density polymer-based integrated electrode apparatus of claim 1 for capturing an image and transmitting the image into an eye to a brain, the apparatus including a video camera that captures the image and sends the image to the eye and through separate metal traces in separate arms made of a poly(dimethylsiloxane) and said central electrode body made of a poly(dimethylsiloxane) to the brain.

* * * * *